United States Patent
Boese

(10) Patent No.: US 8,855,391 B2
(45) Date of Patent: Oct. 7, 2014

(54) OPERATING METHOD FOR AN IMAGING SYSTEM FOR THE TIME-RESOLVED MAPPING OF AN ITERATIVELY MOVING EXAMINATION OBJECT

(75) Inventor: Jan Boese, Eckental (DE)

(73) Assignee: Siemens Aktiengesellschaft, Munich (DE)

( * ) Notice: Subject to any disclaimer, the term of this patent is extended or adjusted under 35 U.S.C. 154(b) by 1218 days.

(21) Appl. No.: 12/381,856

(22) Filed: Mar. 17, 2009

(65) Prior Publication Data

US 2009/0252378 A1  Oct. 8, 2009

(30) Foreign Application Priority Data

Apr. 2, 2008  (DE) .......................... 10 2008 016 892

(51) Int. Cl.
*G06K 9/00*  (2006.01)
*A61B 6/00*  (2006.01)
*A61B 19/00*  (2006.01)

(52) U.S. Cl.
CPC .............. *A61B 6/481* (2013.01); *A61B 6/4441* (2013.01); *A61B 6/504* (2013.01); *A61B 6/5264* (2013.01); *A61B 6/541* (2013.01); *A61B 2019/5289* (2013.01); *A61B 6/503* (2013.01)
USPC ....................................................... 382/131

(58) Field of Classification Search
CPC ................................ A61B 6/504; A61B 5/055
USPC ................................................. 382/128, 131
See application file for complete search history.

(56) References Cited

U.S. PATENT DOCUMENTS

| | | | | |
|---|---|---|---|---|
| 5,782,762 A | * | 7/1998 | Vining | 600/407 |
| 6,408,201 B1 | * | 6/2002 | Foo et al. | 600/410 |
| 6,950,542 B2 | * | 9/2005 | Roesch et al. | 382/128 |
| 7,912,259 B2 | * | 3/2011 | Arditi et al. | 382/128 |

(Continued)

FOREIGN PATENT DOCUMENTS

| | | |
|---|---|---|
| DE | 102004048209 B3 | 9/2005 |
| DE | 102005016472 A1 | 10/2006 |
| DE | 102006030811 A1 | 1/2008 |
| WO | WO 2006119623 A1 | 11/2006 |

OTHER PUBLICATIONS

Gibson et al., "Coronary and Myocardial Angiography; Angiographic Assessment of Both Epicardial and Myocardial Perfusion", Circulation 2004, vol. 109, Issue 25; Jun. 29, 2004, pp. 3096-3105; Magazine; 2004.

(Continued)

Primary Examiner — Matthew Bella
Assistant Examiner — Dennis Rosario

(57) ABSTRACT

The invention relates to an operating method for an imaging system for the time-resolved mapping of an iteratively moving examination object. First recordings of the object are generated by the imaging system from various angles while simultaneously recording a phase signal. Multiple static 3D-image data sets corresponding to a sequence of defined phases are reconstructed from the first recordings. Three-dimensional motion fields are calculated from the 3D-image data sets, by which two 3D-image data sets are mapped onto one another. Second recordings of the object are generated by the imaging system from various angles while simultaneously recording a phase signal. 3D-image data sets from the second recordings in a previously determined reference phase of the phase signal using the motion fields is generated which is a sequence of motion-compensated 3D-image data sets.

13 Claims, 2 Drawing Sheets

(56) References Cited

U.S. PATENT DOCUMENTS

| | | | |
|---|---|---|---|
| 8,036,437 B2 * | 10/2011 | Arditi et al. | 382/128 |
| 8,055,050 B2 * | 11/2011 | Roessl et al. | 382/131 |
| 8,411,915 B2 * | 4/2013 | Wischmann et al. | 382/128 |
| 8,644,910 B2 * | 2/2014 | Rousso et al. | 600/436 |
| 2006/0067459 A1 | 3/2006 | Boese et al. | |
| 2006/0133564 A1 | 6/2006 | Langan et al. | |
| 2006/0285632 A1 * | 12/2006 | Boese et al. | 378/8 |
| 2007/0030945 A1 | 2/2007 | Boese et al. | |
| 2007/0092055 A1 | 4/2007 | Vives et al. | |
| 2008/0013675 A1 | 1/2008 | Boese et al. | |

OTHER PUBLICATIONS

Montes et al., "Analysis of Time Resolution in Dynamic Computed Tomography for Perfusion Studies", Montes et al.; IEEE Nuclear Science Symposium Conference Record, Rome, Italy, Oct. 16-22, 2004; Others; 2004.

Lauritsch et al., "Towards Cardiac C-Arm Computed Tomography", IEEE Transactions on Medical Imaging, vol. 25, No. 7, Jul. 2006, pp. 922-934; Others; 2006.

Blondel et al., "Reconstruction of Coronary Arteries From a Single Rotational X-Ray Projection Sequence" IEEE Transactions on Medical Imaging, vol. 25, No. 5, May 2006; pp. 653-663; Magazine; 2006.

* cited by examiner

OPERATING METHOD FOR AN IMAGING SYSTEM FOR THE TIME-RESOLVED MAPPING OF AN ITERATIVELY MOVING EXAMINATION OBJECT

CROSS REFERENCE TO RELATED APPLICATIONS

This application claims priority of German application No. 10 2008 016 892.0 filed Apr. 2, 2008, which is incorporated by reference herein in its entirety.

FIELD OF THE INVENTION

The present invention relates to an operating method for an imaging system for the time-resolved mapping of an iteratively moving examination object, in particular to a method for simultaneous time-resolved cardiac imaging and perfusion imaging by means of an angiography apparatus, of which a C-arm apparatus will stand as an example here, and a corresponding computer program and a data carrier on which this computer program is stored. The invention also relates to an imaging system.

BACKGROUND OF THE INVENTION

Angiography apparatuses or systems are used for interventions in the heart in order, by means of X-ray imaging, to monitor these interventions. Angiography apparatuses of this kind typically have a C-shaped arm, on one end of which an X-ray source and on the other end of which an associated X-ray detector is mounted. The C-arm is freely pivotable about a patient couch and allows by this means the recording of two-dimensional real-time X-ray images (fluoroscopic recordings) of the patient from a wide variety of viewing angles.

Traditionally, angiography systems generate simple projected X-ray images on which structures such as heart shadows, guide wires, catheters and contrast-agent-filled catheters can be recognized. For some years, angiography systems have, through rotation of the C-arm around the patient, also been able to generate CT-like 3D images, on which soft tissue can be viewed three-dimensionally. The representation options are, however, restricted to the morphology, i.e. the structure, of the regions examined.

This invention deals with the problem of determining by means of angiography systems information about perfusion of the cardiac muscle. This problem is of special interest because a suitable method can, in contrast to the established methods for perfusion measurement (MR, SPECT, PET), be applied during an intervention.

Tissue perfusion or perfusion can be determined with a multiplicity of radiological methods such as e.g. magnetic resonance tomography (MR), computed tomography (CT), ultrasound or positron emission tomography (PET). Most of the methods are based on a contrast-agent bolus being injected and the concentration of the contrast agent being examined as a function of time.

A prerequisite for this is rapid image recording so as to be able to trace the passage of the bolus. The recording of images at an interval of approx. 1 to 2 seconds is typically required for this purpose. Angiography systems can generate projection recordings at such speeds without problem, and in this way trials relating to perfusion measurement in the heart have already been proposed, as disclosed in C. Michael Gibson and Albert Schömig: Coronary and Myocardial Angiography: Angiographic Assessment of Both Epicardial and Myocardial Perfusion. Circulation 109; pages 3096 to 3105, 2004. The projection methods have many disadvantages, however, in particular, an accurate assignment of an area in the projected image to the corresponding area of the three-dimensional anatomy is not possible.

There are also ideas for the measurement of perfusion by means of three-dimensional image recording in angiography systems (see DE 10 2006 030 811 A1, US 2007/0092055 A1 and Montes, P.; Lauritsch, G., "Analysis of time resolution in dynamic computed tomography for perfusion studies", Nuclear Science Symposium Conference Record, 2004 EEEE, vol. 7, no., pages 4195 to 4199, Vol. 7, 16-22 Oct. 2004). For the 3D-recording, the C-arm of the angiography system has to rotate around the patient over an angular range of more than 180°, which restricts the time resolution to typically 4 to 5 seconds. The issue in these studies is therefore the problem of obtaining, despite the relatively poor time resolution, meaningful perfusion measurement values in the 3D recording by means of angiography systems.

However, the known methods are restricted to static, or in any case almost static, organs. In moving organs such as the heart, disruptions, referred to as artifacts, occur in the 3D images and therefore also in the perfusion images on account of the motion of the heart.

Methods also exist for mapping the heart in 3D by means of angiography systems (see DE 10 2004 048 209 B3, DE 10 2005 016 472 A1 and G. Lauritsch, J. Boese, L. Wigström, H. Kemeth, and R. Fahrig, "Towards Cardiac C-Arm Computed Tomography", IEEE Transactions on Medical Imaging, vol. 25, pages 922 to 934, 2006); however, these require multiple 3D recordings simply for the ECG gating used for suppressing the motion of the heart. This adversely affects the temporal resolution so severely that perfusion measurements are not possible. ECG gating in this context means the use of a defined method with which by using the ECG signal in the 3D reconstruction a series of 3D images of a defined phase can be assigned as a result.

The fundamental problem of cardiac perfusion measurements is that to date by means of multiple rotational passes of the C-arm only either the cardiac phases can be taken into account by means of ECG gating or the temporal course of a contrast-agent bolus can be examined without ECG gating. Doing both simultaneously has previously not been possible.

SUMMARY OF THE INVENTION

The object underlying the present invention is therefore to provide an operating method for an imaging system for the time-resolved mapping of an iteratively moving examination object as well as a corresponding computer program, optionally stored on a data medium, with which the disadvantages known from the prior art can be eliminated, and improved measurement results, in particular cardiac perfusion measurements, are possible.

This object is achieved by the independent claims.

Advantageous developments of the invention are the subject matter of the dependent claims.

The basic idea of this invention is consequently firstly to record a data set knowing the phase position of the examination object. From this, the motion field is then extracted. With this information, a second recording with multiple rotational passes can then be motion-compensated. In this way, the motion of the examination object can be calculated or corrected out. The term "phase" here designates a defined point in time within the motion cycle of the iteratively moving object. A motion field is a three-dimensional mapping matrix, with the aid of which a three-dimensional image data set recorded at a defined point in time can in each case be converted into a different image data set for a different point in time.

The invention thus provides a new data acquisition and reconstruction method with which, especially in the preferred application of cardiac imaging, both cardiac phases and contrast agent dynamics can be captured simultaneously. In this way, it is possible for the first time to represent contrast agent dynamics by means of angiography systems without having to accept "blurring" of the image over all the cardiac phases. This makes the meaningful deployment of C-arm-based perfusion measurement in cardiology meaningfully possible for the first time.

In contrast to other perfusion measurement methods, the invention has the advantage that it can be used directly during interventions in the heart. No transportation of the patient to a different system (such as e.g. MR, PSECT) is necessary, which simplifies the workflow and makes it possible for information relating to perfusion to be taken into account directly during the treatment process.

According to a preferred embodiment, multiple rotational passes of the imaging system, which are time-correlated with the phase signal and proceed over an angular range of greater than 180°, are used in the step relating to the reconstruction of three-dimensional image data sets. Details are specified in DE 10 2005 016 472 A1. A good level of accuracy of the motion field can be achieved by this means with just two rotational passes. The method is very fast and efficient if no more than four rotational passes are used.

The term "rotational pass" means that a C-arm is pivoted over an angular range of (at least) 180°+fan angle, with 50 to 500 images being recorded as a rule. The "fan angle" equals the angle at which the X-ray source emits the X-ray radiation and as a rule stands at about 20°.

It is, however, also possible to determine the motion fields using different methods. For example, symbolic reconstruction methods are known which can determine the motion field from a single rotational pass. An example of this, in which the motion field can, however, only be estimated, is described in: C. Blondel, G. Malandain, R. Vaillant, and N. Ayache: Reconstruction of Coronary Arteries From a Single Rotational X-Ray Projection Sequence, IEEE TMI, Vol. 25, no. 5, 2006. A problem here can be that this method is not generally applicable, but can be deployed only under certain conditions such as with high-contrast objects.

The filtered back projection method has proven to be a practical and readily implementable method for the reconstruction of three-dimensional image data sets.

For the calculation of the image fields, it is preferable to use an elastic image registration of two consecutive three-dimensional image data sets. In contrast to rigid image registration, in which two three-dimensional volumes are mapped on one another by means of rotation and translation only, with elastic image registration, a distortion such as for example zooming can also be employed.

The method according to the invention is preferably applied in cardiac imaging with ECG gating with contrast-agent administration. It is also preferable to use, as an imaging system, a C-arm angiography system as a medical X-ray system. In one variant, the two projection recording steps can then also be combined and (at least partially) proceed simultaneously during a single contrast-agent injection. Since a perfectly homogeneous contrast is not required, a transition can be made after recording by means of some rotational passes without ECG gating in the fourth step seamlessly to rotational passes with ECG gating in the first step, and, if required, further rotational passes without ECG gating can be added at the end.

The administration of contrast agent can be automated and standardized, whereby, synchronized with the start of the first step, a contrast agent and, synchronized with the start of the fourth step, a contrast-agent bolus are injected by an automatic injector. Typically, the contrast agent is injected here such that a complete, homogeneous contrast is present during the first step and during the fourth step only a brief contrast-agent bolus is administered which can then, for the purposes of perfusion measurement, be tracked over time.

From the motion-compensated image data sets, a temporal dynamic of the contrast-agent injection can then be calculated in a simple manner, and from the temporal dynamic of the contrast-agent injection the tissue perfusion is calculated.

The imaging system according to the invention for the time-resolved mapping of an iteratively moving examination object comprises a radiator and a detector, which are arranged opposite one another in relation to their pivoting axis and the examination object, for generating first and second projection recordings of the examination object from various angles. The imaging system comprises furthermore a phase detection unit for recording a phase signal which indicates the current phase of iterative motion of the examination object at the time of the first and second projection recordings and a control and evaluation system for controlling the imaging system. The control and evaluation system is designed such that it firstly controls the radiator and the detector for the image recording appropriately and secondly evaluates the recorded images in accordance with one of the methods described hereinabove.

BRIEF DESCRIPTION OF THE DRAWINGS

The invention will be described in detail below with the aid of a preferred exemplary embodiment and with reference to the drawings, in which.

DETAILED DESCRIPTION OF THE INVENTION

The invention will be described below with the aid of a preferred embodiment of a method and a corresponding apparatus for simultaneous time-resolved cardiac imaging and perfusion imaging by means of C-arm CT. Since the heart moves as a rule only approximately and not perfectly periodically, the expression "iterative" is used here.

Figure 3:
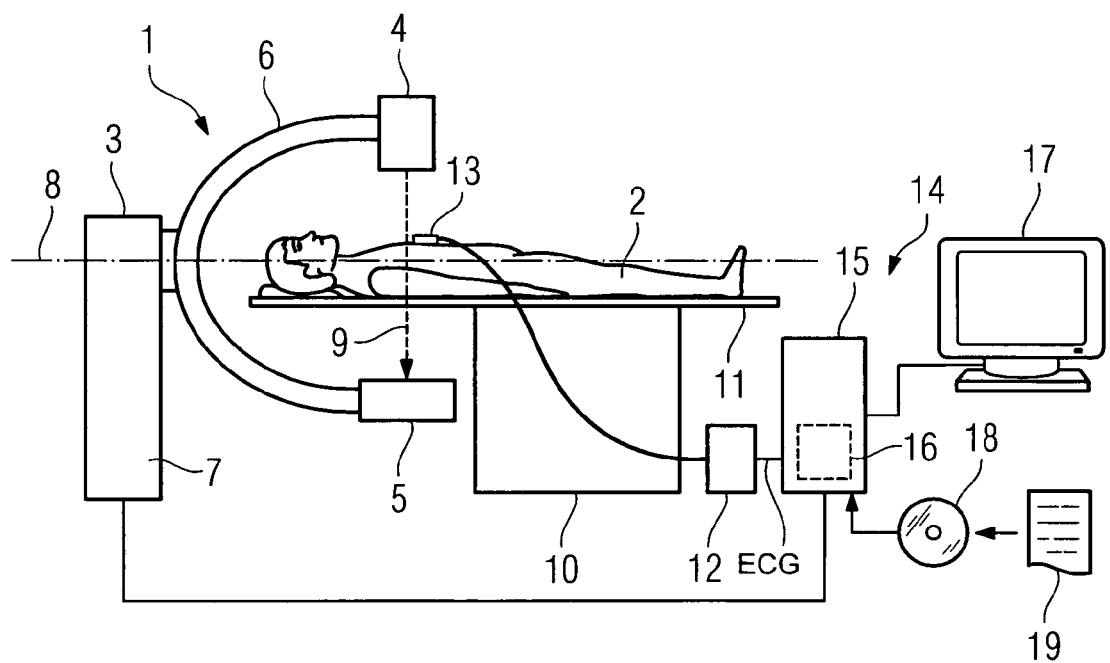
FIG. 3 shows schematically an inventively designed C-arm installation on which the operating method according to the invention can be executed.

Represented schematically in FIG. 3 is an apparatus 1 for generating a three-dimensional image data set of an object. The apparatus 1 is an X-ray tomograph, in particular a 3D rotational angiography system. The object to be examined is the chest region, in particular the heart, of a patient 2.

The apparatus 1 comprises a recording unit 3 with an X-ray source 4 and an X-ray detector 5. X-ray source 4 and X-ray detector 5 are attached opposite one another to the ends of a so-called C-arm 6. The C-arm 6 is in turn rotatably mounted about an isocentric axis 8 approximately centrally on a stand 7. The X-ray source 4 and the X-ray detector 5 are, through pivoting of the C-arm 6 relative to the stand 7 rotatable such that a central beam 9 of the X-ray radiation emitted by the X-ray source 4 in the direction of the X-ray detector 5 can be pivoted within a recording plane perpendicular to the isocentric axis 8 in any projection angle of at least 180° relative to the surrounding space, the central beam 9 being aligned continuously with the isocentric axis.

The appliance 1 comprises furthermore a patient table 10 with a table top 11, on which the patient 2 is placed during an examination such that the longitudinal axis of his body is approximately in alignment with the isocentric axis 8 of the recording unit 3. The table top 11 is for the examination insertable into the opening of the C-arm 6 such that the region of the body of the patient 2 to be examined comes to lie between X-ray source 4 and X-ray detector 5.

The appliance 1 comprises furthermore an ECG unit 12 with a number of ECG sensors 13, which are fastened in a known manner to the body of the patient 2 for recording an electrocardiogram (ECG), i.e. an electrical signal reproducing the cardiac activity of the patient 2.

The appliance 1 comprises furthermore a control and evaluation system 14. The control and evaluation system 14 comprises a data processing system 15, in which are implemented, in addition to operating and control functions (not shown in detail), a read device for a computer program 19 stored on a data medium 18 such as e.g. a CD or a USB stick, and an evaluation unit 16 for generating a three-dimensional (3D) image data set of the examined body region of the patient 2. The control and evaluation system 14 comprises furthermore input/output means 17, such as e.g. screen, keyboard, mouse or such like for the inputting of control instructions and for the displaying of state variables, examination results, etc.

In the course of the method carried out by the appliance 1 digital image data is fed to the evaluation unit 16 by the recording unit 3. Furthermore, an ECG signal ECG of the patient 2 is fed to the evaluation unit 16 from the ECG unit 12.

Figure 2:
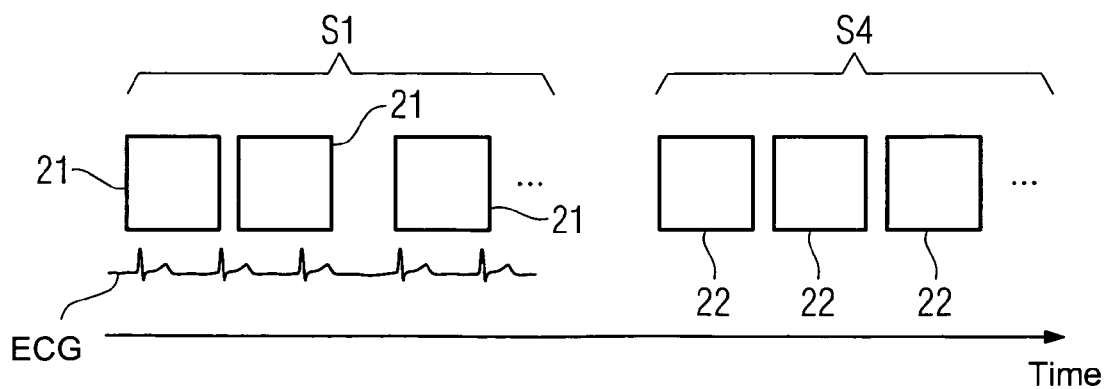
FIG. 2 shows schematically a representation of the two steps of generating projection recordings with and then without ECG gating, but while recording an ECG phase signal.

In a first step S1, first projection recordings 21 of the heart are generated from various angles in two passes or rotational passes by the C-arm system and stored, as shown in FIG. 2. For a 3D reconstruction, it is necessary for a C-arm to execute a rotational pass over an angular range of (at least) 180°+fan angle, with 50 to 500 images being recorded as a rule. At the same time, the ECG signal is recorded which indicates the current phase of the iterative (ideally periodic) motion of the heart at the time of the first projection recordings 21. An example of the execution of this step and of the C-arm system suitable for carrying out all the projection recordings is specified in DE 10 2005 016 472 A1 and does not therefore need to be discussed further, the invention not being restricted hereto. Synchronously with step 1, a contrast agent is administered in order to improve the image quality, for example to increase the light/dark contrast.

Figure 1:
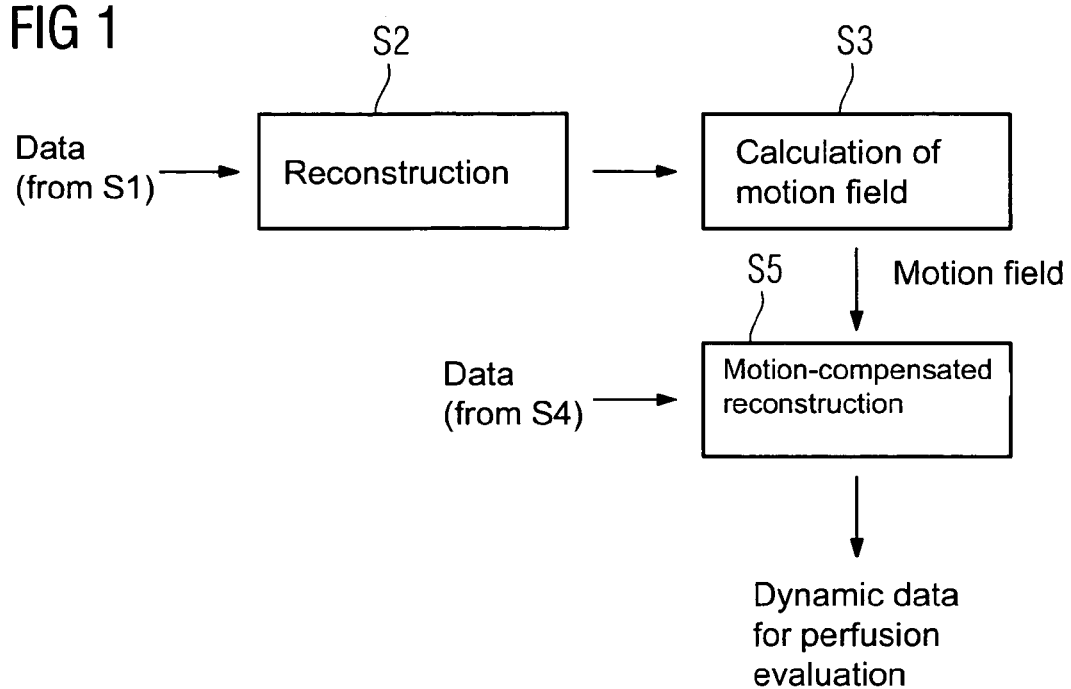
FIG. 1 shows schematically a flow diagram which portrays the flow of an inventive operating method for time-resolved cardiac perfusion measurement.

Then, as shown in FIG. 1, in a second step S2 multiple, at least approximately static, three-dimensional image data sets corresponding to a sequence of defined phases are reconstructed from the first projection recordings 21 and stored. "Approximately static" is used here because there is never a perfect static representation, but only an approximation with a defined time window. A static representation is provided when images from different rotational passes in precisely the same phase respectively are used for the 3D image reconstruction. Therefore, for the approximate representation, in each case the images in the particular phase are used which match most closely the defined phase. From this sequence of three-dimensional image data sets, in a third step S3 three-dimensional motion fields are calculated, by means of which two such three-dimensional image data sets can be mapped onto one another in each case. Such a motion field represents a three-dimensional mapping matrix with the aid of which a three-dimensional image data set recorded at a defined time can respectively be converted or motion-compensated into a different image data set for a different time. The corresponding three-dimensional motion fields can, however, also be combined into a single four-dimensional motion field.

Subsequently, in a fourth step S4 second projection recordings 22 of the heart from various angles are generated and stored in a desired number of, generally, two to four, more if desired, rotational passes of the C-arm system. At the same time, the ECG signal is recorded which indicates the current phase of the motion of the heart at the time of the second projection recordings 22. These projection recordings 22 are then, in a fifth step S5, reconstructed and simultaneously motion-compensated using the motion fields, and this is done in a reference phase of the ECG signal, for which the diastole of the heart is mostly used. A sequence of motion-compensated three-dimensional image data sets can be generated in this way.

Synchronously with step 4, a contrast-agent bolus is administered. Its tracking over time enables measurement of the perfusion of blood vessels of the heart.

This invention consequently contains in other words a new data acquisition procedure which consists of multiple passes of the C-arm around the patient, and a new data reconstruction method.

In the 3D recording of the heart with ECG gating, in step S1 at least one, and preferably consecutive, rotational passes is/are carried out, whereby, if necessary, waiting times dependent on the current cardiac phase are observed in order to achieve for a given projection angle different phases where possible and thereby optimum coverage of all the projection angles for a defined cardiac phase.

The acquisition method used in the invention functions as follows (cf. FIG. 2):
In a first step S1, preferably two or more rotational passes with ECG gating are executed.
In a fourth step S4, a number of rotational passes is executed while recording the ECG-phase signal.

In tandem with this procedure, the injection of a contrast-agent bolus takes place. This can be administered manually or preferably by an automatic injector. The contrast agent is typically injected such that a completely homogeneous contrast is present during step S1, and during step S4 only a brief contrast-agent bolus is administered which can then be tracked over time for perfusion measurement purposes.

The reconstruction method used in the invention functions as follows (cf. FIG. 1):
Firstly, in a second step S2, the data or the recordings of the first acquisition step S1 for a number of different cardiac phases are fed for 3D reconstruction such that a 4D data set is produced.
From this data set, motion fields are calculated in a third step S3. Motion fields preferably represent three-dimensional mapping matrixes, each matrix indicating the temporal motion of each voxel occurring during the heartbeat.
With the motion fields now provided, in a fifth step S5 the recordings of the second acquisition step S4 can now be reconstructed in a motion-compensated manner (i.e. in relation to a defined reference cardiac phase such as preferably the diastole).
A data set corresponding to the reference cardiac phase is produced, from which perfusion parameters such as e.g. the area under the bolus curve or the time to the maximum of the bolus curve can be derived. This data set is "dynamic" to the extent that it is a sequence of three-dimensional data sets, on which the inflow of the bolus can be tracked, even if all the data sets show the heart in the motion state of the reference cardiac phase. As a result of the motion-compensated reconstruction in the fifth step, projection recordings from phases which do not correspond to the reference cardiac phase can also be used for calculating data sets which represent the heart in the reference cardiac phase.

It should be noted that the features of the invention described with reference to the embodiment shown, such as for example the precise design of the motion fields or the number of rotational passes executed in the individual steps, may also be present in other embodiments, unless specified otherwise or ruled out per se for technical reasons.

The invention claimed is:

1. An operating method for an imaging system for time-resolved mapping of an examination object moving periodically with various phases, comprising:
   generating a first set of projection recordings of the examination object by the imaging system at a first set of different angles using ECG gating;
   synchronously injecting a contrast agent at a start of the recording of the first set of projection recordings;
   simultaneously recording a first phase signal indicating a first set of phases of the periodically moving examination object at time of recording the first set of the projection recordings;
   reconstructing a first set of static three-dimensional image data sets in the first set of phases from the first set of the projection recordings;
   calculating three-dimensional motion fields corresponding to defined reference phases from the first set of the three-dimensional image data sets by which two of the first set of the three-dimensional image data sets are mapped onto one another;
   generating a second set of projection recordings of the examination object by the imaging system at a second set of different angles without using ECG gating during said generating the second set of projection recordings;
   simultaneously recording a second phase signal indicating a second set of phases of the periodically moving examination object at time of recording the second set of the projection recordings;
   injecting a contrast-agent bolus synchronized at a start of the recording of the second set of the project recordings after the contrast agent injected at the start of the recording of the first set of projection recordings presents homogeneously;
   generating a sequence of motion-compensated three-dimensional image data sets in the defined reference phases by reconstructing a second set of three-dimensional image data sets from the second set of the projection recordings using the three-dimensional motion fields,
   wherein the three-dimensional motion fields indicate a temporal motion of the periodically moving examination object, and
   wherein the second set of projection recordings are recorded from phases that do not correspond to the defined reference phases of the first set of the projection and the three-dimensional motion fields, and
   wherein the second set of projection recordings are converted into the first set of projection recordings for the defined reference phases to calculate the sequence of motion-compensated three-dimensional image data sets using the three-dimensional motion fields, and
   dynamically tracking an inflow of the contrast-agent bolus injected at the start of the recording of the second set of projection recordings over time on the sequence of motion-compensated three-dimensional image data sets.

2. The operating method as claimed in claim 1, wherein the first set of the static three-dimensional image data sets are reconstructed by recordings of multiple rotational passes of the imaging system that is time-correlated with the first phase signal and runs over an angular range of greater than 180°.

3. The operating method as claimed in claim 1, wherein the first set and the second set of the three-dimensional image data sets are reconstructed by filtered back projection.

4. The operating method as claimed in claim 1, wherein the motion fields are calculated by an elastic image registration of two consecutive three-dimensional image data sets from the first set of the three-dimensional image data sets.

5. The operating method as claimed in claim 1, wherein the first set and the second set of the projection recordings are executed one after another during a single contrast-agent injection.

6. The operating method as claimed in claim 1, wherein the imaging system is a medical X-ray system.

7. The operating method as claimed in claim 6, wherein the medical X-ray system is a C-arm angiography system.

8. The operating method as claimed in claim 1, wherein the examination object is a heart of a live body.

9. The operating method as claimed in claim 8, wherein the first set and the second set of phases are cardiac phases of the heart and the first and the second phase signal is an ECG signal of the heart.

10. The operating method as claimed in claim 1, wherein a temporal dynamic of the contrast agent bolus is calculated from the motion-compensated three-dimensional image data sets.

11. The operating method as claimed in claim 10, wherein a tissue perfusion is calculated from the temporal dynamic of the contrast-agent bolus.

12. A non-transitory data medium having a computer program executable in a computer for an imaging system for time-resolved mapping of an examination object moving periodically with various phases, comprising:
   a computer program subroutine that:
      reads:
         a first set and a second set of projection recordings of the examination object generated by the imaging system at various angles, wherein the first set of projection recordings is generated using ECG gating and the second set of projection recordings is generated without using ECG gating during said generating the second set of projection recordings, and
         a first phase signal and a second phase signal indicating a first set and a second set of phases of the periodically moving examination object at time of recording the first set and the second set of the projection recordings;
      reconstructs a first set of static three-dimensional image data sets in the first set of phases from the first set of the projection recordings;
      calculates three-dimensional motion fields corresponding to defined reference phases from the first set of the three-dimensional image data sets by which two of the first set of the three-dimensional image data sets are mapped onto one another; and
      generates a sequence of motion-compensated three-dimensional image data sets in the defined reference phases by reconstructing a second set of three-dimensional image data sets from the second set of the projection recordings using the three-dimensional motion fields, wherein the three-dimensional motion fields indicate a temporal motion of the periodically moving examination object, and wherein the second set of projection recordings are recorded from phases that do not correspond to the first set of the projection and the defined reference phases of the three-dimensional motion fields, and wherein the second set of projection recordings are converted into the first set of projection recordings for the defined reference phases to calculate the sequence of motion-compensated three-dimensional image data sets using the three-dimensional motion fields, wherein a contrast agent is synchronously injected at a start of the recording of the first set of projection recordings, wherein a contrast-agent bolus is synchronously injected at a start of the recording of the second set of the project recordings after the contrast agent injected at the start of the recording of the first set of projection recordings presents homogeneously, and dynamically tracks an inflow of the contrast-agent bolus injected at the start of the recording of the second set of projection recordings over time on the sequence of motion-compensated three-dimensional image data sets.

13. An imaging system for a time-resolved mapping of an periodically moving examination object, comprising:

a radiator;

a detector arranged opposite with the radiator that generates a first and a second set of projection recordings of the examination object at various angles, wherein the first set of projection recordings is generated using ECG gating and the second set of projection recordings is generated without using ECG gating during said generating the second set of projection recordings;

a phase-detection unit that records a first phase signal and a second phase signal indicating a first set and a second set of phases of the periodically moving examination object at time of recording the first set and the second set of the projection recordings; and a control and evaluation system that:

reconstructs a first set of static three-dimensional image data sets in the first set of phases from the first set of the projection recordings;

calculates three-dimensional motion fields corresponding to defined reference phases from the first set of the three-dimensional image data sets by which two of the first set of the three-dimensional image data sets are mapped onto one another; and generates a sequence of motion-compensated three-dimensional image data sets in the defined reference phases by reconstructing a second set of three-dimensional image data sets from the second set of the projection recordings using the three-dimensional motion fields, wherein the three-dimensional motion fields indicate a temporal motion of the periodically moving examination object, and wherein the second set of projection recordings are recorded from phases that do not correspond to the first set of the projection and the defined reference phases of the three-dimensional motion fields, and wherein the second set of projection recordings are converted into the first set of projection recordings for the defined reference phases to calculate the sequence of motion-compensated three-dimensional image data sets using the three-dimensional motion fields, wherein a contrast agent is synchronously injected at a start of the recording of the first set of projection recordings, wherein a contrast-agent bolus is synchronously injected at a start of the recording of the second set of the project recordings after the contrast agent injected at the start of the recording of the first set of projection recordings presents homogeneously, and dynamically tracks an inflow of the contrast-agent bolus injected at the start of the recording of the second set of projection recordings over time on the sequence of motion-compensated three-dimensional image data sets.

* * * * *